(12) United States Patent
Sasing

(10) Patent No.: US 8,172,842 B2
(45) Date of Patent: May 8, 2012

(54) CERVICAL PLATE SYSTEM HAVING AN INSERTABLE ROTATING ELEMENT

(75) Inventor: Jude L. Sasing, Quezon (PH)

(73) Assignee: Orthopaedic International, Inc., Cabuyao, Laguna (PH)

( * ) Notice: Subject to any disclaimer, the term of this patent is extended or adjusted under 35 U.S.C. 154(b) by 882 days.

(21) Appl. No.: 11/496,349

(22) Filed: Jul. 31, 2006

(65) Prior Publication Data

US 2008/0027439 A1 Jan. 31, 2008

(51) Int. Cl.
*A61B 17/56* (2006.01)
*A61B 17/58* (2006.01)
*A61B 17/80* (2006.01)
*A61F 2/30* (2006.01)

(52) U.S. Cl. ......................................................... 606/71
(58) Field of Classification Search ................ 606/71, 606/289, 301, 286, 288, 307, 282, 287
See application file for complete search history.

(56) References Cited

U.S. PATENT DOCUMENTS

| | | | | |
|---|---|---|---|---|
| 3,741,205 A | * | 6/1973 | Markolf et al. | 606/291 |
| 4,029,091 A | * | 6/1977 | von Bezold et al. | 606/33 |
| 5,380,327 A | * | 1/1995 | Eggers et al. | 606/287 |
| 5,735,850 A | * | 4/1998 | Baumgartner et al. | 606/288 |
| 6,129,730 A | * | 10/2000 | Bono et al. | 606/291 |
| 6,193,721 B1 | | 2/2001 | Michelson | |
| 6,340,362 B1 | * | 1/2002 | Pierer et al. | 606/71 |
| 6,398,783 B1 | | 6/2002 | Michelson | |
| 6,454,771 B1 | | 9/2002 | Michelson | |
| 6,458,133 B1 | | 10/2002 | Lin | |
| 6,599,290 B2 | * | 7/2003 | Bailey et al. | 606/86 B |
| 6,764,489 B2 | * | 7/2004 | Ferree | 606/279 |
| 7,276,070 B2 | * | 10/2007 | Muckter | 606/71 |
| 7,537,596 B2 | * | 5/2009 | Jensen | 606/280 |
| 2002/0026194 A1 | * | 2/2002 | Morrison et al. | 606/71 |
| 2004/0102776 A1 | * | 5/2004 | Huebner | 606/69 |
| 2004/0220570 A1 | * | 11/2004 | Frigg | 606/69 |
| 2005/0033298 A1 | * | 2/2005 | Hawkes et al. | 606/61 |
| 2005/0043736 A1 | * | 2/2005 | Mathieu et al. | 606/73 |
| 2006/0089648 A1 | * | 4/2006 | Masini | 606/69 |
| 2006/0276794 A1 | * | 12/2006 | Stern | 606/69 |

FOREIGN PATENT DOCUMENTS

| | | |
|---|---|---|
| DE | 100 39 767 A1 | 7/2001 |
| WO | WO 95/35067 | 12/1995 |
| WO | WO 02/00124 | 1/2002 |
| WO | WO 03/055401 | 7/2003 |
| WO | WO 2006/113257 | 10/2006 |

OTHER PUBLICATIONS

Moftakhar, et al., "Anterior cervical plates: a historical perspective", Neurosurg Focus 16(1): Article 8, 2004.
Haid, et al., "The Cervical Spine Study Group Anterior Cervical Plate Nomenclature", Neurosurg Focus 12(1), 2002.

* cited by examiner

*Primary Examiner* — Thomas C. Barrett
*Assistant Examiner* — David Bates
(74) *Attorney, Agent, or Firm* — Kagan Binder, PLLC

(57) ABSTRACT

A cervical plate system which includes a cervical plate having a thickness between a top surface and an opposite bottom surface, and at least one slot extending through the thickness of the plate. The system further includes a first rotating element positionable within a first slot of the cervical plate, the first rotating element including at least one threaded hole, and at least one bone screw insertable into the at least one threaded hole of the first rotating element.

13 Claims, 3 Drawing Sheets

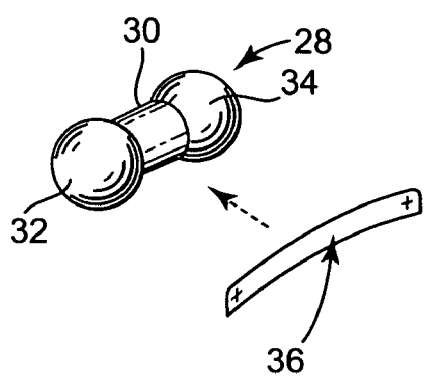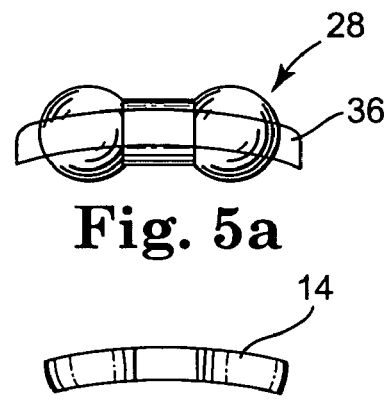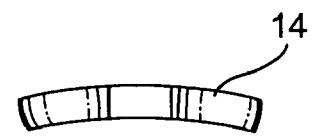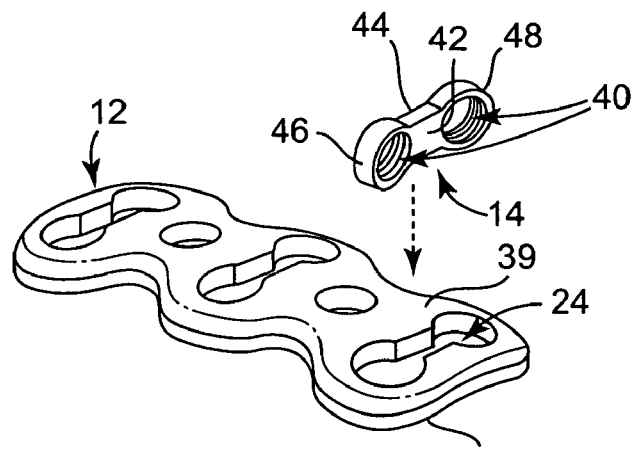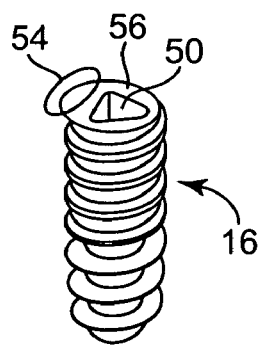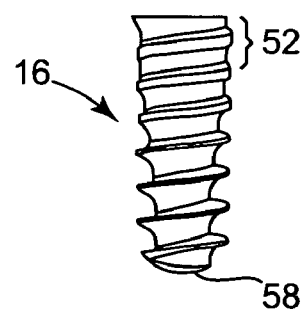

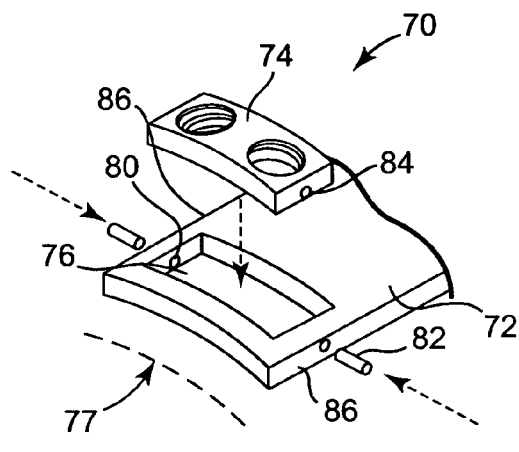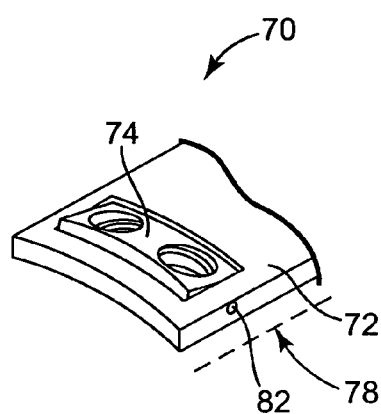
Fig. 9          Fig. 10
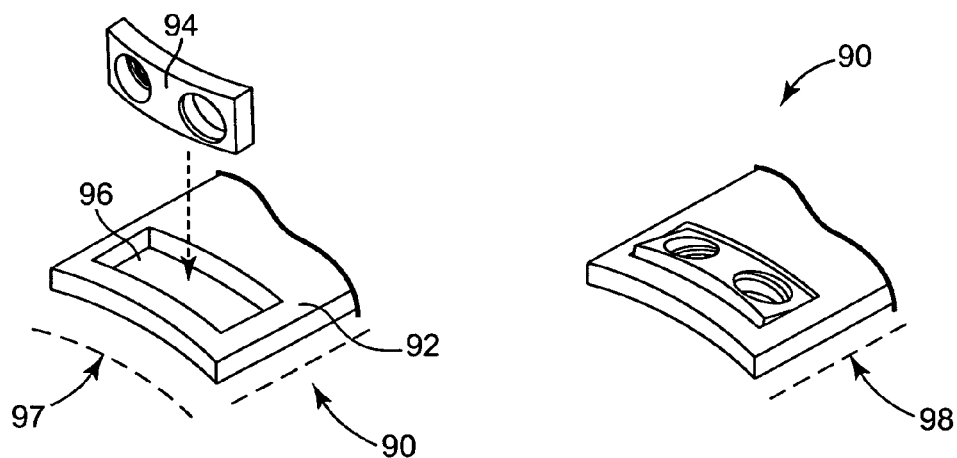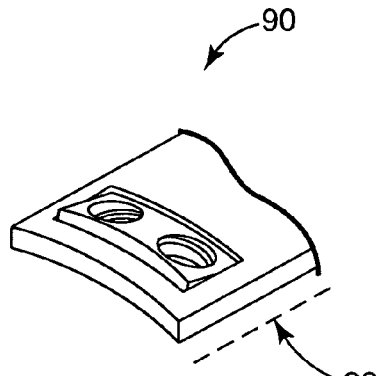
Fig. 11          Fig. 12

CERVICAL PLATE SYSTEM HAVING AN INSERTABLE ROTATING ELEMENT

TECHNICAL FIELD

The present invention relates to spinal plates for surgical implantation in a patient. The invention more particularly relates to a cervical plate system for fixation of the cervical spine, where such cervical plate system is configured to prevent certain movement of the securing screws once the system is implanted.

BACKGROUND OF THE INVENTION

Anterior cervical plates can be used for fixation of the cervical spine. Some of the first anterior cervical plate systems used simple plates and screws, such as the Caspar plate system commercially available from Aesculap Inc., of Center Valley, Pa. However, these plates did not have any mechanism for locking the bone screws to the plate, which thereby created a potential situation where one or more of the screws connecting the plate to the spine could back out of its opening in the spine. These systems have subsequently been modified and now most anterior cervical plating systems available in the market employ some kind of screw locking mechanism or anti-screw back out mechanism to prevent the screw from backing out of the bone and plate. They also allow the screws to move relative to the plate either in rotation, translation, or a combination of both rotation and translation.

Some cervical plate systems use a locking element that is engaged once the screw has been inserted into the bone. One example of such a system is commonly known in the industry as a "Codman plate", which is available from Johnson & Johnson of New Brunswick, N.J. The Codman plate generally includes a cam built into a plate, which can be rotated 180 degrees to engage the head of the screw and prevent it from backing out. This cam only prevents the screw from backing out, and does not prevent it from moving or rotating relative to the plate. Another example of a cervical plate system that includes a locking element is the ABC system, which is commercially available from Aesculap Inc., of Center Valley, Pa. With this system, once a bone screw has been inserted into the bone, a tiny locking screw is advanced into the head of the screw, thereby making the head expand and engage the hole in the plate to prevent the screw from backing out of the plate. In the Vuelock system, which is commercially available from Biomet, Inc. of Warsaw, Ind., a retaining ring that is incorporated into the plate snaps into place once a bone screw is fully inserted, thereby preventing it from backing out of the plate.

In other cervical plate systems, drill guides align screw holes relative to a cervical plate, but screw insertion is performed manually. Since the screws used in cervical plating are typically quite small (e.g., around 4 mm in diameter), it is difficult to determine by feel when the screw is adequately tightened and/or when it has reached its maximum seating depth. Thus, there is a risk with these systems of over-tightening the screw into the bone, which can cause the threads to strip the bone and thereby lose their thread purchase.

The Window cervical plate system, which is commercially available from A-Spine Inc. of Taipei, Taiwan, generally includes a bone screw that engages or meshes with the cervical plate. The cervical plate of the Window system includes a longitudinal slot that corresponds to each bone screw and which meshes with the bone screw threads. The plate itself does not have threads, so meshing with the bone screw is achieved through a thinned out portion of the slot being "captured" between the head and the threaded portion of each bone screw. Relative motion between the plate and the bone screw is mainly translational and possibly includes limited rotation/angulation. A cervical plate system with these general features is also described in U.S. Pat. No. 6,458,122, titled "Spinal Fixation and Retrieval Device". There is a need, however, to provide an improved cervical plate system that provides flexible rotation capabilities for the screws and that prevents bone screws from backing out once the system is implanted.

SUMMARY OF THE INVENTION

Unlike some of the prior art cervical plate systems, the current invention does not involve a locking element that needs to be engaged after a bone screw is inserted in order to keep the bone screw from backing out of the cervical plate. Instead, the surgical procedure is simplified and involves less components, since screw locking is automatically achieved once the screw is fully inserted and tightened. Also, the systems of this invention do not involve tiny components, which can be difficult to manipulate in surgery. Accuracy of the screw trajectories is also ensured since the screws are threaded into the rotating elements, which are incorporated into the plate itself. The present invention also provides a rotating element that is threaded to match the bone screw threads. Meshing between the threads is therefore exact, and the screw can be tightened onto the rotating element to thereby provide more secure locking between the components.

Another advantage of the current invention is that the possibility of stripping the threads in the bone is minimized or eliminated. In particular, this situation is eliminated using the devices and methods of the present invention because the maximum engagement of the screw threads and the threads on the rotating element determine the maximum seating depth of the screw. Thus, the screw will tighten into the rotating element, and not into the bone.

In general, the present invention includes a device for stabilizing the cervical spine. It is composed of a plate with two or more slots, a rotating element contained inside each slot, and two bone screws that correspond to each slot and are threadable into the rotating element. Each rotating element can rotate relative to the top and bottom surfaces of the plate. The rotating element has two threaded holes having threads that match the threads of the bone screw. When each bone screw is threaded into the bone, the threads engage the rotating element, locking the bone screw to the rotating element. This prevents the screws from backing out, and at the same time allows the screws to rotate relative to the plate (through the rotating element), thereby allowing "bone graft settling". The rotating element has outer surfaces that correspond to inner surfaces of the slot in the cervical plate to allow insertion of the rotating element when oriented perpendicular to the top and bottom surfaces of the cervical plate. However, this same rotating element is not removable from the slot when it is oriented or rotated in a generally non-perpendicular orientation relative to the top and bottom surfaces of the cervical plate. In addition, when the bone screws are threaded into the rotating element so that they protrude through the bottom of the cervical plate, the portion of the screw that extends beyond the bottom of the plate can contact the bottom of the plate if the rotating element is rotated a certain amount toward its perpendicular or insertion orientation. In this way, the inserted bone screws serve as a stop or obstruction to rotation of the rotating element back to its perpendicular orientation in which the rotating element would be removable from the cervical plate in which it is inserted.

In one aspect of the invention, a cervical plate system is provided, which comprises a cervical plate having a thickness between a top surface and an opposite bottom surface, and at least one slot extending through the thickness of the plate. The system further includes a first rotating element positionable within a first slot of the cervical plate, the first rotating element comprising at least one threaded hole, and at least one bone screw insertable into the at least one threaded hole of the first rotating element. The rotating element can have a maximum length that is at least slightly larger than a width of the first slot at a top surface of the cervical plate. The first rotating element can further have a first end and an opposite second end, wherein at least one of the first and second ends has a convex profile, and the first slot in which the first rotating element is positioned can comprise a concave profile at its first and second ends to cooperatively engage with at least one of the first and second ends of the first rotating element. Each bone screw may be positionable so that it extends beyond the bottom surface of the cervical plate and so that each bone screw is in a fixed position relative to the rotatable element and is rotatable relative to the cervical plate. Further, the bone screws may be threaded along their entire length and in at least one embodiment will comprise a head portion that is enlarged relative to a base portion of the screw for preventing rotation of the bone screw beyond a predetermined position.

In another aspect of the invention, a rotating element is provided for use within a cervical plate of a cervical plate system, the cervical plate having a thickness between a top and an opposite bottom surface and at least one slot extending through the thickness of the plate. The rotating element is rotatably positionable within a slot of the cervical plate about a first axis and the rotating element comprises at least one threaded hole through its thickness. This rotating element further comprises a bone screw threaded into each of the at least one threaded holes in the rotating element.

BRIEF DESCRIPTION OF THE DRAWINGS

The present invention will be further explained with reference to the appended Figures, wherein like structure is referred to by like numerals throughout the several views, and wherein:

FIG. 4 is a perspective view of a shaped element consisting of a cylinder with spherical ends, along with a schematic shape that will be superimposed on the shaped member to create the interior shape of the slots in the cervical plate of the invention;

FIG. 5a is a front view of the shaped element of FIG. 4, with a schematic shape superimposed upon it;

FIG. 5b is a front view of a rotating element of the invention, which is the portion of the shaped element that essentially matches the schematic shape of FIG. 5a;

FIG. 6 is a perspective exploded perspective view of the cervical plate and rotating element of FIG. 2;

FIG. 7 is a perspective view of one embodiment of a bone screw of the present invention;

FIG. 8 is a front view of the bone screw of FIG. 7;

FIG. 9 is an exploded perspective view of a portion of another exemplary embodiment of a cervical plate system of the invention;

FIG. 10 is an assembled perspective view of the cervical plate system of FIG. 9;

FIG. 11 is an exploded perspective view of a portion of another exemplary embodiment of a cervical plate system of the invention; and FIG. 12 is an assembled perspective view of the cervical plate system of FIG. 11.

DETAILED DESCRIPTION OF THE PREFERRED EMBODIMENTS

Figure 1:
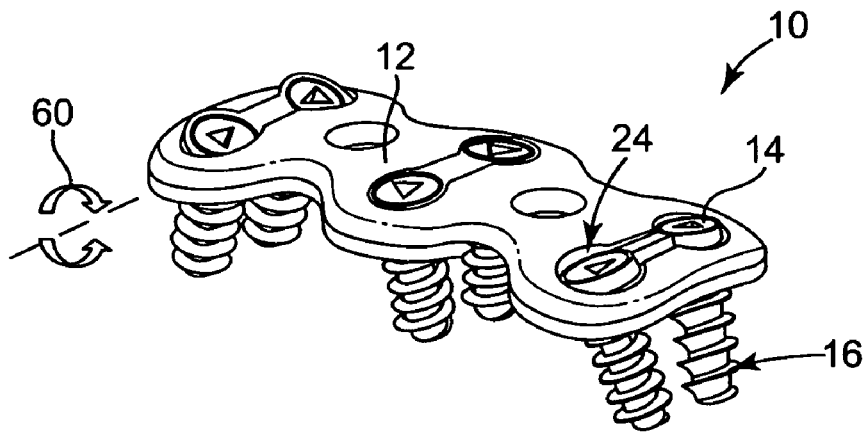
FIG. 1 is a perspective view of one embodiment of a cervical plate system of the present invention.
Figure 2:
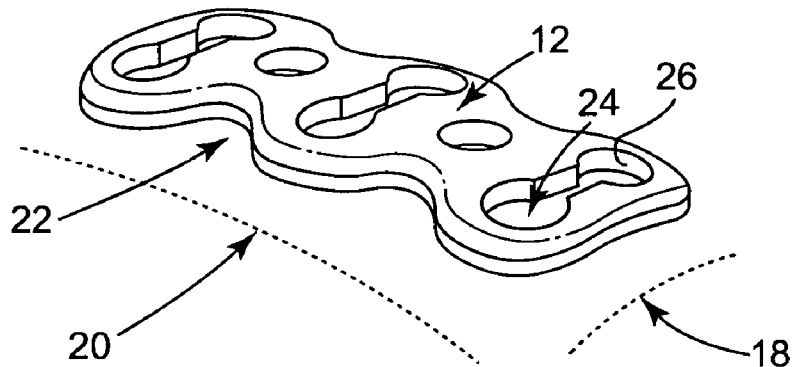
FIG. 2 is a perspective view of the cervical plate of the cervical plate system of FIG. 1.
Figure 3:
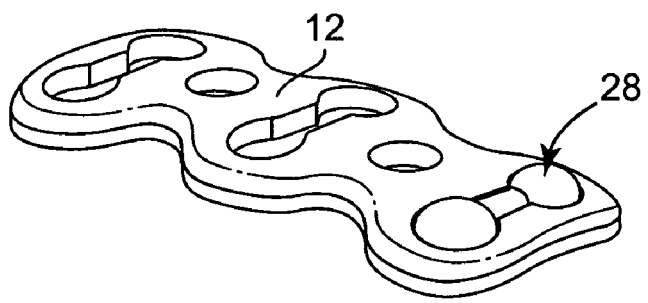
FIG. 3 is a perspective view of the cervical plate of FIGS. 1 and 2, including a shaped element having a cylinder with spherical ends positioned within a slot of the cervical plate, which demonstrates the shape characteristics of a rotating element of the invention.

Referring now to the Figures, wherein the components are labeled with like numerals throughout the several Figures, and initially to FIGS. 1-3, one preferred configuration of a cervical plate system 10 is illustrated. System 10 generally includes a cervical plate 12, at least one rotating element 14, and one or more bone screws 16 for each corresponding rotating element 14. Cervical plate 12 includes a first curvature 18 that is designed to closely match the curvature of the vertebrae in the cervical spine and a second curvature 20 that is designed to closely match the lordotic curvature of the cervical spine. The cervical plate 12 is generally rectangular, and is provided with generally smooth and/or curved edges to minimize discomfort and injury to the patient that might occur with sharp or rough edges. However, the periphery of the plate may have a different general shape, such as oval or elliptical, or may have a more irregular shape. In any case, the cervical plate preferably includes at least one recessed area 22 provided between adjacent wider areas of the plate 12. These recessed areas 22 are portions of cervical plate 12 with less strength than the remainder of the plate, which can facilitate additional contouring of the cervical plate 12 during surgery, if desired. When recessed areas 22 are provided, they may be smooth, relatively semi-circular areas, as shown, or may include a wide variety of shapes, such as semi-elliptical, semi-oval, rectangular (e.g., wide or narrow slots), and the like. In general, these recessed areas 22 provide portions of the cervical plate 12 that correspond with areas between adjacent spinal segments into which the bone screws will be attached.

Cervical plate 12 further includes at least one slot or elongated opening 24 that extends across a portion of the width of the cervical plate 12. Each slot 24 is positioned to match the approximate locations of the vertebrae to which the plate 12 will be attached. While the cervical plate 12 of the figures is illustrated as having three such slots 24 along its length, the cervical plates of the invention may instead include more or less than three slots 24, each of which will correspond with a vertebral body in the patient to which bone screws will attach. Each slot or opening 24 has an interior surface 26 that has a shape that is approximated as a portion of a cylinder having spheres at both ends, which is described further with reference to a 3-dimensional element 28 in FIG. 4.

In particular, element 28 includes a cylinder 30, a first sphere 32 positioned at one end of cylinder 30, and a second sphere 34 positioned at the opposite and of cylinder 30. The center point of each of the spheres 32, 34 is approximately aligned with a longitudinal axis of the cylinder 30, although they can be at least slightly offset from each other. As illustrated in FIG. 4, a shape or template 36 is translated or overlaid onto the element 28 to establish the size and shape characteristics of a certain slot or opening 24. In particular, the shape 36 has a curvature in one direction that roughly matches the first curvature 18 illustrated in FIG. 2 (i.e., the approximate curvature of the vertebrae in the cervical spine). A slice or section of the element 28 having this shape 36 is taken through its center to calculate or predetermine the shape and size of the slots 24 in the plate 12. When viewed from the top of the plate 12, the shape of the slots 24 will be the same as the outer shape of the element 28. This shape 36 that is modeled using the element 28 can be cut into the cervical plate 12 in the desired locations along the length of the plate 12. Of course, the shape of the interior surface 26 can be calculated or determined using computer modeling or other similar techniques, thus, it is understood that the shape 36 may instead be molded as a part of the original configuration of the cervical plate 12, or may be formed into the plate 12 using a variety of known manufacturing techniques. In any case, shape 36 has a height that is generally the same as the thickness of the cervical plate 12 into which the slots or openings 24 are formed.

Cervical plate system 10 further includes a rotating element 14 corresponding to each of the slots 24. With reference to FIGS. 3, 5a, and 5b, the shape of the rotating elements 14 is described. In particular, the same element 28 described above relative to the slots 24 is also used as the template for determining the shape of the rotating elements 14. For illustration purposes, FIG. 3 shows an entire element 28 positioned within one of the slots 24, which is different than the final shape of the rotating elements 14. Element 28 is sized and shaped to be at least slightly smaller than the slot in which it is positioned so that it fits in the opening and rotate within it. However, the actual rotating elements 14 of the invention will not protrude from the top and bottom surfaces of the plate 12 as shown in this figure.

To determine the shape of the rotating element 14, the shape 36, which is the same shape discussed above relative to the slot 24, is translated or overlaid onto the element 28, as shown best in FIG. 5a. That is, the rotating element 14 will essentially have an exterior shape that matches the shape of a slice taken out of the element 28, as shown in FIG. 5b. The rotating elements 14 may be formed in a number of ways, such as by cutting the element 14 from a shaped element 28, or by molding or otherwise forming the element 14 into a shape that is modeled as a section of the shaped element 28 in FIGS. 5a and 5b. Due to the shaping of the slot 24, the inner surface 26 of the each slot 24 is concave along its edges and surfaces when viewed as a cross-section through the thickness of the plate 12. Further, the first and second ends 46, 48 of rotating element 14 may be described as being convex when viewed from the top to the bottom of plate 12. In this way, the slot 24 will be able to cooperatively engage with the rotating element 14, as described below.

Referring now to FIG. 6, the rotating elements 14 further include two threaded holes 40 that match the threads of the screws 16, as will be discussed in further detail below. The axes of the two threaded holes 40 converge toward a concave or bottom surface 38 of the plate 12. This convergence improves the pullout strength and prevents the plate 12 from being pulled out of the bone after the assembly 10 is implanted in a patient.

In order to assemble the cervical plate assembly 10 prior to implantation of the system in a patient, a rotating element 14 will preferably be positioned within each of the slots 24 that will be involved in the spinal fixation. That is, a cervical plate 12 may have at least one slot 24 with no rotating element 14 positioned therein, if desired, such as if it were determined that all of the vertebral bodies adjacent to slots 24 did not need to be attached to the plate 12. However, it is preferable that the cervical plate 12 chosen for a particular patient has a number of slots 24 that correspond to the number of vertebral bodies to which the device will be attached. In any case, due to the geometry of the slots 24 and rotating elements 14 described above, the opening of the slot 24 at the top surface 39 of plate 12 will be at least slightly smaller across its width than the widest part of the rotating element 14. That is, due to the cylindrical/spherical shape of both the rotating element 14 and the slot 24, the periphery of the slot 24 at the top surface of the cervical plate 12 will have a slightly smaller width than the rotating element 14 that will be inserted therein. In order to position the rotating element 14 inside the slot 24, the rotating element 14 will be oriented so that its front and back surfaces 42, 44, respectively, are generally perpendicular to a top surface 39 of the cervical plate 12, as shown in FIG. 6. In this position, the interference between the rotating element 14 and slot 24 is only at its first and second ends 46, 48. Thus, it is relatively easy to push the rotating element 14 from the top into the slot 24 as shown in FIG. 6, although there will be at least a slight amount of resistance due to the sizes of the rotating element 14 and its corresponding slot 24.

Once the rotating element 14 is inserted into the slot 24 in this perpendicular orientation, the rotating element 14 can be rotated within the slot 24 until its back surface 44 is essentially flush with the top surface 39 of cervical plate 12 and its front surface 42 is essentially flush with the bottom surface 38 of the cervical plate 12. When the rotating element 14 is oriented in this way (as shown in FIG. 1, for example), there is interference both in the cylindrical and spherical portions of the rotating element 14 and the slot 24 so that the rotating element 14 cannot be removed from the slot 24. In order to remove the rotating element 14 from the slot 24, the rotating element 14 can be rotated until its surfaces 42, 44 are generally perpendicular to the top surface of the cervical plate 12, then the element 14 can be pressed outwardly until it disengages from the surfaces of the slot 24.

Referring now to FIGS. 7 and 8, the bone screws 16 used in the cervical plate system 10 include an opening 50 at a first end 56 for engagement with a driving tool, such as a screwdriver. In this embodiment, the opening 50 is shown as generally triangular in shape, and would therefore require a cooperatively shaped driving tool that can securely engage with the opening 50. The opening 50 may instead have a different shape, such as circular, rectangular, elliptical, slot-shaped, and the like, any of which will need a driving tool having a corresponding shape for manipulation of the bone screw 16. The opening 50 can extend into the central portion of the bone screw 16 along its longitudinal length for any desired hole depth, although it is preferable that the depth is large enough to allow for secure engagement between a driving tool and the opening 50.

The bone screws 16 are preferably threaded along substantially the entire length of their outer surfaces. The thread pattern further preferably includes tapering threads (i.e., having a decreasing minor diameter) when moving from the first end 56 towards the second end 58 of the bone screw 16, which is the end that penetrates the bone. Because the threads in bone screw 16 extend along the entire length of the screw, the screw "head" 52 is the portion of the screw that engages the rotating element 14 when the bone screw 16 is fully inserted. The thread has a constant pitch, but the minor diameter is increasing towards the head 52. The head 52 further includes an enlarged portion 54, which acts as a stopper to stop the screw 16 from rotating, thereby preventing the screw 16 from going all the way through the rotating element 14 when inserted therein.

Referring again to FIG. 1, the rotating elements 14 may rotate or pivot in a direction generally indicated by arrows 60 where the rotating elements 14 may rotate 360 degrees within the slots 24 when no screws 16 are inserted into the rotating elements 14. However, once the screws 16 are inserted into the slot 24, the degree of rotation of the rotating element 14 will be limited due to interference between the bone screws 16 and the bottom of the cervical plate 12. This interference prevents the rotating element 14 from rotating to the position where it can be removed from the cervical plate 12 (i.e., generally perpendicular to the top surface of cervical plate 12).

During surgical application of the invention, screw holes are drilled into the cervical vertebral bodies of the patient to which the cervical plate system 10 will be attached. The cervical plate system 10, which includes a rotating element 14 positioned within each of the corresponding slots 24 in the cervical plate 12, is then placed on top of the cervical spine of the patient in the general desired implantation location. A threaded drill sleeve is then threaded into one of the threaded holes 40 of the rotating element 14. The orientation of the screw hole to be made in the vertebra of the patient will be determined by rotating or pivoting the rotating element 14 within its respective slot 24, which will also provide the corresponding orientation of the drill sleeve attached to it. Once this desired orientation of the screw hole is determined, a drill is inserted into the drill sleeve and a screw hole is drilled into the vertebra. After these screw holes in the bone are drilled, the holes are tapped using a bone tap that is inserted through the threaded holes 40 of the rotating element 14. In accordance with the invention, the helix of the threads in the bone will coincide with the helix of the threads in the threaded holes 40 of the rotating element 14, which will prevent the plate from being urged away from the vertebra as the bone screw 16 is inserted. This is accomplished because the rotating element 14 with threaded holes 40 is positioned relative to the vertebra when the tap is first threaded through the rotating element 14, and then the tap is immediately threaded into the adjacent bone. In this way, the thread in the bone will be a continuation of the threads in the threaded hole 40 of the adjacent rotating element 14.

In another exemplary embodiment of the invention, a pin connection between the rotating element and the plate can also be used instead of the shape of the slot and the rotating element described above, as is illustrated with a portion of a cervical plate system 70 in FIGS. 9 and 10. As shown, cervical plate system 70 generally includes a cervical plate 72, at least one rotating element 74, and one or more bone screws (not shown) for each corresponding rotating element 74. The portion of plate 72 shown has a periphery that is generally rectangular in shape, but it may instead have a different peripheral configuration, such as having a similar periphery to the cervical plate 12 of FIG. 1. That is, this plate 72 also preferably includes at least one recessed or reduced-width area provided between wider areas of the plate 72 where the rotating elements 74 are positioned. The cervical plate 72 includes a first curvature 77 that is designed to closely match the curvature of the vertebrae in the cervical spine and a second curvature 78 that is designed to closely match the lordotic curvature of the cervical spine. The rotating element 74 preferably, but not necessarily, also includes curvatures that match the first and second curvatures 77, 78.

Cervical plate 72 further includes at least one slot or elongated opening 76 that extends across a portion of the width of cervical plate 72. Each slot 76 is positioned to match the approximate locations of the vertebrae to which the plate will be attached. Each slot 76 further includes a small aperture or hole 80 that extends through at least one of the interior sides of the slot and through the plate 72 to at least one of its outer edges 86. The hole 80 is sized to accept a hinge pin 82 so that when the rotating element 74 is positioned within the slot 76, a hinge pin 82 can be inserted into the hole 80 at one or both of the outer edges 86 of the plate 72 and into a hole 84 in one or both edges of the rotating element 74. As shown in FIG. 10, the rotating element 74 is then able to rotate or pivot about the hinge pin or pins 82.

Another exemplary embodiment of the invention is illustrated in FIGS. 11 and 12 as a cervical plate system 90. As shown, cervical plate system 90 generally includes a cervical plate 92, at least one rotating element 94, and one or more bone screws (not shown) for each corresponding rotating element 94. The portion of plate 92 shown has a periphery that is generally rectangular in shape, but it may instead have a different peripheral configuration, such as having a similar periphery to the cervical plate 12 of FIG. 1. The cervical plate 92 includes a first curvature 97 that is designed to closely match the curvature of the vertebrae in the cervical spine and a second curvature 98 that is designed to closely match the lordotic curvature of the cervical spine. The rotating element 94 preferably, but not necessarily, also includes curvatures that match the first and second curvatures 97, 98.

Cervical plate 92 further includes at least one slot or elongated opening 96 that extends across a portion of the width of cervical plate 92. Each slot 96 is positioned to match the approximate locations of the vertebrae to which the plate will be attached. In addition, slot 96 is preferably sized and shaped similarly to the slot described relative to the embodiment of FIG. 1 in that the slot 96 shown in FIG. 12 is able to accept a rotating element 94 that can rotate therein, without requiring any additional elements to hold the rotating element 94 in the slot 96. However, the periphery of the rotating element 94 of this embodiment is generally rectangular in shape, in contrast to the shape of the rotating element illustrated in FIG. 1. In that regard, the outer periphery of the rotating elements of the invention may take a wide variety of peripheral shapes to accommodate a variety of peripheral shapes that may be provided for their corresponding slots. In any case, as illustrated in FIG. 11, in order to assemble the cervical plate system 90, the rotating element 94 is preferably oriented so that its top and bottom faces are generally perpendicular to the top face of plate 92. The rotating element 94 is pressed into the slot 96 until it engages with the inner surfaces of slot 96 and is able to rotate within the slot 96.

Other alternatives in implementing the basic concept of the present invention include using one rotating element for each bone screw instead of one rotating element for two bone screws as discussed above. Still another variation of this invention would be to use other locking elements to lock the screw to the rotating element (e.g., a retaining ring) instead of using the threads on the screw and on the rotating element.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A cervical plate system, comprising:
   a cervical plate having a top surface, an opposite bone-contacting bottom surface having a predetermined contour based on a predetermined portion of the cervical spine, a slot extending through the cervical plate, a first edge and an opposite second edge located on opposite sides across a width of the cervical plate, and a first convex curvature between the first and second edges;

a rotating element positionable within the slot of the cervical plate and rotatable relative to the cervical plate when positioned within the slot of the cervical plate, the rotating element comprising first and second spaced apart threaded holes, wherein each of the threaded holes comprises a central axis, wherein the central axes of the first and second holes extend through the slot and converge toward each other below the bottom surface of the cervical plate, and wherein the rotating element comprises a convex curvature across its width that generally matches the first convex curvature of the cervical plate; and a first bone screw insertable into the first threaded hole of the rotating element and a second bone screw insertable into the second threaded hole of the rotating element.

2. The cervical plate system of claim 1, wherein the rotating element has a maximum length that is at least slightly larger than a width of the slot at the top surface of the cervical plate.

3. A cervical plate system, comprising:

a cervical plate having a top surface, an opposite bone-contacting bottom surface having a predetermined contour based on a predetermined portion of the cervical spine, and a slot extending through the cervical plate;

a rotating element positionable within the slot of the cervical plate and rotatable relative to the cervical plate when positioned within the slot of the cervical plate, the rotating element comprising first and second spaced apart threaded holes, wherein each of the threaded holes comprises a central axis, wherein the central axes of the first and second holes extend through the slot and converge toward each other below the bottom surface of the cervical plate, wherein the rotating element has a first end and an opposite second end, and wherein at least one of the first and second ends has a convex profile; and a first bone screw insertable into the first threaded hole of the rotating element and a second bone screw insertable into the second threaded hole of the rotating element.

4. The cervical plate system of claim 3, wherein at least one of a first end and a second end of the slot in which the rotating element is positionable comprises a concave profile to cooperatively engage with at least one of the first and second ends of the rotating element.

5. The cervical plate system of claim 1, wherein each bone screw is positionable so each bone screw extends beyond the bottom surface of the cervical plate and so each bone screw is in a fixed position relative to the rotatable element and is rotatable relative to the cervical plate.

6. The cervical plate system of claim 1, wherein the first bone screw is insertable in the first threaded hole of the rotating element, the second bone screw is insertable in the second threaded hole of the rotating element, and the first and second bone screws are fixed relative to each other and rotatable relative to the cervical plate about a first axis.

7. The cervical plate system of claim 1, wherein each of the first and second bone screws is threaded along the entire length of each bone screw.

8. The cervical plate system of claim 7, wherein each of the first and second bone screws comprises a head portion that is enlarged relative to a base portion of the screw for preventing rotation of the bone screw beyond a predetermined position.

9. The cervical plate system of claim 1, wherein each of the first and second bone screws comprises a head portion, a tip opposite the head portion, and a minor diameter that increases from the tip toward the head portion.

10. The cervical plate system of claim 1, wherein each of the first and second bone screws comprises threads having a helix that matches a helix of threads in a bone into which each of the bone screws will be threaded.

11. The cervical plate system of claim 1, further comprising multiple slots in the cervical plate and a corresponding number of rotating elements positionable within each of the multiple slots and rotatable relative to the cervical plate when positioned within each of the multiple slots of the cervical plate.

12. The cervical plate system of claim 1, wherein the rotating element can rotate 360 degrees within the slot of the cervical plate when no bone screws are inserted into the first and second threaded holes.

13. The cervical plate system of claim 1, wherein the cervical plate further comprises a first end and a second end, each of which extends between the first and second edges of the plate, and a second convex curvature between the first and second ends of the cervical plate.

* * * * *